United States Patent
Gerdt et al.

(12)

(10) Patent No.: US 6,687,424 B1
(45) Date of Patent: Feb. 3, 2004

(54) SENSING PAD ASSEMBLY EMPLOYING VARIABLE COUPLER FIBEROPTIC SENSOR

(75) Inventors: David W. Gerdt, Charlottesville, VA (US); Martin C. Baruch, Charlottesville, VA (US); Charles Adkins, Earlysville, VA (US)

(73) Assignee: Empirical Technologies Corporation, Charlottesville, VA (US)

( * ) Notice: Subject to any disclaimer, the term of this patent is extended or adjusted under 35 U.S.C. 154(b) by 0 days.

(21) Appl. No.: 09/763,718

(22) PCT Filed: Aug. 24, 1999

(86) PCT No.: PCT/US99/19259

§ 371 (c)(1),
(2), (4) Date: Feb. 26, 2001

(87) PCT Pub. No.: WO00/10447

PCT Pub. Date: Mar. 2, 2000

Related U.S. Application Data (60) Provisional application No. 60/126,339, filed on Mar. 26, 1999, and provisional application No. 60/097,618, filed on Aug. 24, 1998.

(51) Int. Cl.[7] ................................................. G02B 6/26
(52) U.S. Cl. ............................. 385/12; 385/13; 385/31; 385/32; 385/39
(58) Field of Search ......................... 385/12, 13, 31, 385/32, 39, 43, 95, 96

(56) References Cited

U.S. PATENT DOCUMENTS

| | | | |
|---|---|---|---|
| 4,245,648 A | 1/1981 | Trimmer et al. .............. 128/680 |
| 4,545,253 A | 10/1985 | Avicola ........................ 73/655 |
| 4,634,858 A | 1/1987 | Gerdt et al. ................. 250/227 |
| 4,752,141 A | 6/1988 | Sun et al. ..................... 374/161 |
| 4,763,977 A | * 8/1988 | Kawasaki et al. ............. 385/43 |
| 4,862,144 A | 8/1989 | Tao .............................. 340/573 |
| 4,947,859 A | 8/1990 | Brewer et al. ............... 128/715 |
| 5,026,984 A | 6/1991 | Gerdt ....................... 250/227.21 |
| 5,056,884 A | 10/1991 | Quinlan, Jr. .................. 385/13 |
| 5,074,309 A | 12/1991 | Gerdt ........................... 600/528 |
| 5,136,669 A | 8/1992 | Gerdt ............................ 385/39 |
| 5,173,747 A | 12/1992 | Boiarski et al. ............. 356/361 |
| 5,187,366 A | 2/1993 | Hopenfeld ................... 250/302 |
| 5,200,615 A | 4/1993 | Hopenfeld ................... 250/302 |
| 5,222,165 A | 6/1993 | Bohlinger ..................... 385/16 |
| 5,289,256 A | 2/1994 | Gramling ..................... 356/345 |
| 5,303,586 A | 4/1994 | Zhao et al. ................... 73/293 |
| 5,333,217 A | 7/1994 | Kossat .......................... 385/32 |
| 5,339,374 A | 8/1994 | Murphy et al. ................ 385/43 |
| 5,340,715 A | 8/1994 | Slovacek et al. .............. 435/6 |
| 5,343,037 A | 8/1994 | Berkcan ................. 250/227.21 |
| 5,362,971 A | 11/1994 | McMahon et al. .......... 250/577 |
| 5,378,889 A | 1/1995 | Lawrence .............. 250/227.16 |
| 5,394,239 A | 2/1995 | Valette ........................ 356/345 |
| 5,481,922 A | 1/1996 | Washabaugh ................. 73/774 |
| 5,494,798 A | 2/1996 | Gerdt et al. .................... 435/6 |
| 5,525,800 A | 6/1996 | Sanghera et al. ....... 250/339.08 |
| 5,532,493 A | 7/1996 | Hale et al. ................ 250/458.1 |
| 5,535,747 A | 7/1996 | Katakura et al. ....... 128/660.02 |
| 5,649,543 A | 7/1997 | Hosaka et al. |
| 5,671,191 A | 9/1997 | Gerdt .......................... 367/140 |
| 5,684,460 A | 11/1997 | Scanlon ....................... 340/573 |
| 5,699,461 A | 12/1997 | Minemoto et al. ............ 385/12 |
| 5,712,934 A | 1/1998 | Johnson ........................ 385/12 |
| 5,828,798 A | 10/1998 | Hopenfeld .................... 385/12 |

OTHER PUBLICATIONS

Tatterson, Kathleen G., "Optical Acoustic Sensors Could Aid Diagnoses", *Photonics Spectra*, Oct. 1997, pp. 55–56.

* cited by examiner

*Primary Examiner*—John D. Lee
*Assistant Examiner*—Juliana K. Kang
(74) *Attorney, Agent, or Firm*—Miles & Stockbridge P.C.

(57) ABSTRACT

A sensing pad assembly for monitoring acoustic activity or motion of an object supported on the pad utilizes an improved fiberoptic sensor as a pressure transducing element to convert pressure fluctuations due to the acoustic activity or motion to an output that changes in accordance with the pressure fluctuations. The sensor has an improved design that permits deflection of the coupler fusion region without accompanying tension. In a preferred embodiment, the coupler fusion region is arranged substantially in a U-shape so that the fiberoptic leads of the sensor may be located adjacent to each other at one side of the sensor.

68 Claims, 5 Drawing Sheets

SENSING PAD ASSEMBLY EMPLOYING VARIABLE COUPLER FIBEROPTIC SENSOR

CROSS-REFERENCE TO RELATED APPLICATIONS

This application claims the benefit of U.S. Provisional Application Nos. 60/097,618 filed Aug. 24, 1998, and Ser. No. 60/126,339 filed Mar. 26, 1999, both of which are incorporated herein by reference.

BACKGROUND OF THE INVENTION

This invention relates to a sensing pad assembly for monitoring acoustic activity and/or motion of an object supported on the pad. The invention is more particularly concerned with a sensing pad assembly that utilizes an improved variable coupler fiberoptic sensor as a pressure transducing element. The sensing pad is suitable for use in a variety of monitoring applications and is especially useful in systems for continuously monitoring medical patients, or more generally, human subjects.

It is commonplace in medical practice to continuously monitor a patient's vital signs, such as heart rate and respiration rate, for changes that may indicate deterioration of the patient's condition. Continuous monitoring systems typically require the attachment of electrical and/or physical sensors to the patient's body using adhesive or straps. Such sensors are generally uncomfortable to the patient and often limit patient activity due to the presence of the sensors, straps, and associated sensor leads. Moreover, such monitoring systems are subject to false outputs due to unreliability of skin contact with patient movement.

An alternative form of monitoring system has been proposed in which the patient is supported on a sensing pad having an associated pressure transducer that does not contact the patient. Acoustic activity and motion of the patient generate pressure fluctuations in the material of the pad. These fluctuations, which vary in accordance with the parameter or parameters being monitored, propagate through the pad material to the transducer. The transducer then converts them to electrical signals for processing by a monitoring circuit.

Figure 1:
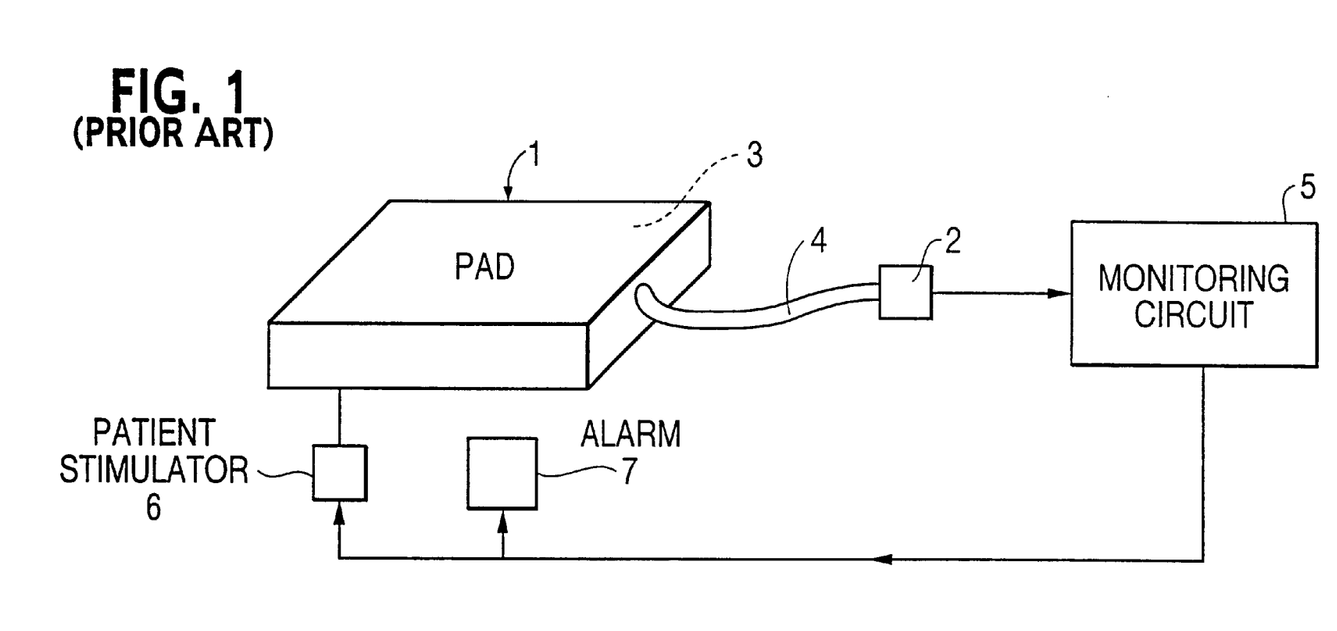
FIG. 1 is a simplified block diagram of a conventional monitoring system using a sensing pad.

U.S. Pat. No. 5,684,460 to Scanlon (hereinafter referred to as "the '460 patent") discloses one example of a monitoring system as just described. FIG. 1 illustrates this system in simplified block diagram form. The system includes a fluid-filled sensing pad 1 adapted to support a patient and to transmit pressure fluctuations due to the patient's acoustic activity or motion to a pressure transducer 2 that converts the pressure fluctuations to an electrical output. The pressure transducer is coupled to the internal fluid medium 3 of the pad via a hose 4. A monitoring circuit 5 monitors the output from the transducer and provides outputs to activate a patient stimulator 6 and an alarm 7 upon the occurrence of predetermined conditions, such as when the transducer output corresponds to no sound and/or movement (below a predetermined threshold) or indicates abnormal activity of the patient.

The sensing pad 1 may be in the form of a fluid-filled mattress or configured for use in some other suitable support such as a vehicle seat or a stroller. Proposed applications of the system for monitoring human subjects include the monitoring of infants at risk for sudden infant death syndrome (SIDS), controlling sleep apnea and snoring, and sensing the onset of sleep for drivers of motor vehicles. Other proposed applications include monitoring machinery for noises and vibrations indicative of atypical operation.

The '460 patent mentions several classes of sensors as being suitable for use as the pressure transducer. Examples include electrical, mechanical, piezoelectric, and fiberoptic sensors.

One type of fiberoptic sensor not explicitly mentioned in the '460 patent, but known to have performance characteristics that are especially well suited for patient monitoring and a variety of other applications, is the variable coupler fiberoptic sensor.

Variable coupler fiberoptic sensors conventionally employ so-called biconical fused tapered couplers manufactured by a draw and fuse process in which a plurality of optical fibers are stretched (drawn) and fused together at high temperature. The plastic sheathing is first removed from each of the fibers to expose the portions for forming the fusion region. These portions are juxtaposed, usually intertwisted one to several twists, and then stretched while being maintained above their softening temperature in an electric furnace or the like. As the exposed portions of the fibers are stretched, they fuse together to form a narrowed waist region—the fusion region—that is capable of coupling light between the fibers. During the stretching process, light is injected into an input end of one of the fibers and monitored at the output ends of each of the fibers to determine the coupling ratio. The coupling ratio changes with the length of the waist region, and the fibers are stretched until the desired coupling ratio is achieved, typically by a stretching amount at which the respective fiber light outputs are equal. The coupler is drawn to such an extent that, in the waist region, the core of each fiber is effectively lost and the cladding may reach a diameter near that of the former core. The cladding becomes a new "core," and the evanescent field of the propagating light is forced outside this new core, where it envelops both fibers simultaneously and produces the energy exchange between the fibers. A detailed description and analysis of the biconical fused tapered coupler has been given by J. Bures et al. in an article entitled "Analyse d'un coupleur Bidirectional a Fibres Optiques Monomodes Fusionnes", Applied Optics (Journal of the Optical Society of America), Vol. 22, No. 12, Jun. 15, 1983, pp. 1918–1922.

Biconical fused tapered couplers have the advantageous property that the output ratio can be changed by bending the fusion region. Because the output ratio changes in accordance with the amount of bending, sensors employing such couplers can be used in virtually any sensing application involving motion that can be coupled to the fusion region. For example, U.S. Pat. No. 5,074,309 to Gerdt discloses the use of such sensors for monitoring cardiovascular sounds including both audible and sub-audible sounds from the heart, pulse, and circulatory system of a patient. Other applications of variable coupler fiberoptic sensors can be found in U.S. Pat. No. 4,634,858 to Gerdt et al. (disclosing application to accelerometers), U.S. Pat. No. 5,671,191 to Gerdt (disclosing application to hydrophones), and elsewhere in the art.

Conventional variable coupler fiberoptic sensors have relied upon designs in which the fiberoptic coupler is pulled straight, secured under tension to a plastic support member and, in the resulting pre-tensioned linear (straight) form, encapsulated in an elastomeric material such as silicone rubber. The encapsulant forms a sensing membrane that can be deflected by external forces to cause bending of the coupler in the fusion region. The bending of the fusion region results in measurable changes in the output ratio of the coupler. The displacement of the membrane can be made sensitive to as little as one micron of movement with a range of several millimeters.

Figure 2:
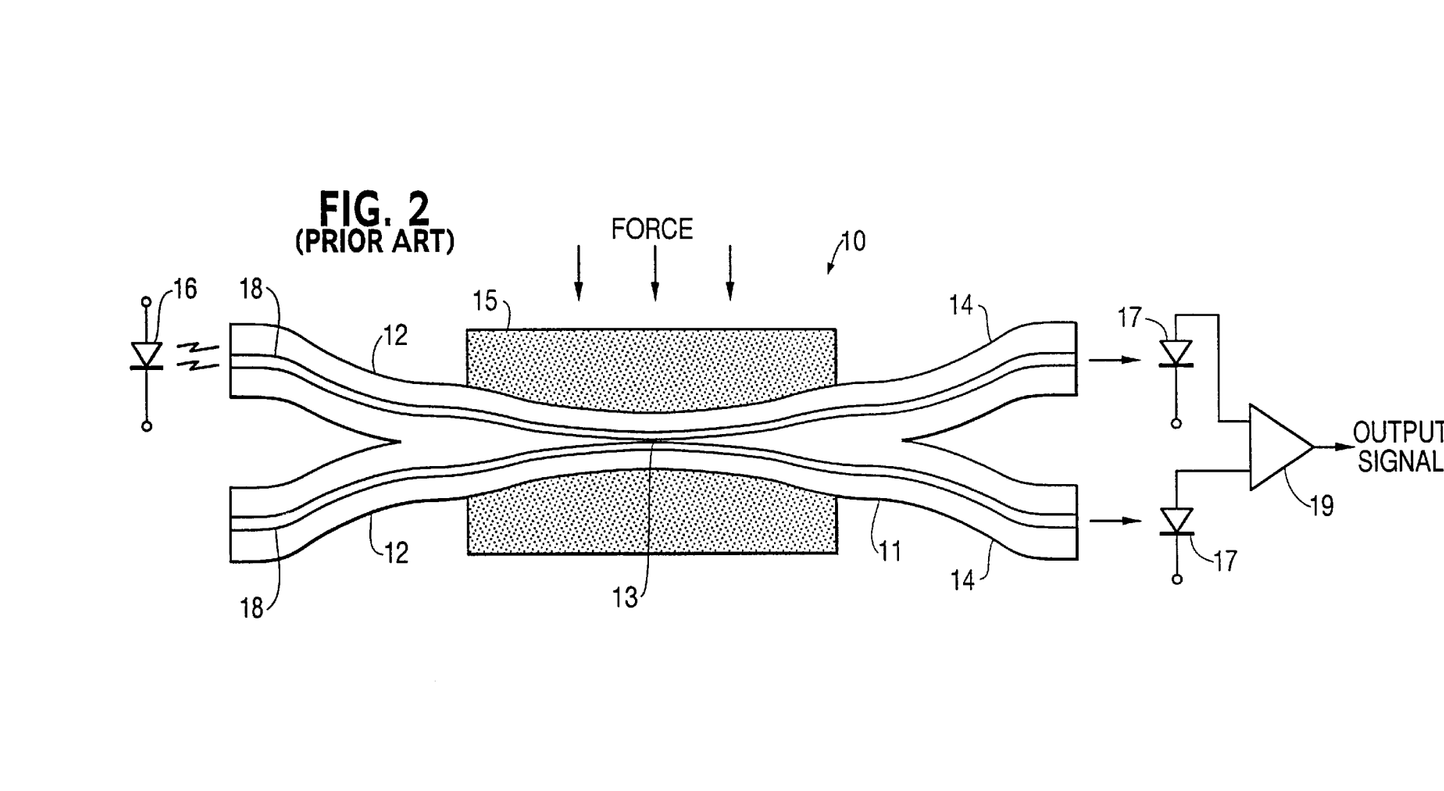
FIG. 2 illustrates the basic construction of a conventional variable coupler fiberoptic sensor.

FIG. 2 of the accompanying drawings illustrates the basic principles of a sensing apparatus including a variable coupler fiberoptic sensor 10 as described above. In the form shown, the sensor 10 includes a 2×2 biconical fused tapered coupler 11 produced by drawing and fusing two optical fibers to form the waist or fusion region 13. Portions of the original fibers merging into one end of the fusion region become input fibers 12 of the sensor, whereas portions of the original fibers emerging from the opposite end of the fusion region become output fibers 14 of the sensor. Reference numbers 18 denote the optical fiber cores. The fusion region 13 is encapsulated in an elastomeric medium 15, which constitutes the sensing membrane. The support member is not shown in FIG. 1.

In practice, one of the input fibers 12 is illuminated by a source of optical energy 16, which may be an LED or a semiconductor laser, for example. The optical energy is divided by the coupler 11 and coupled to output fibers 14 in a ratio that changes in accordance with the amount of bending of the fusion region as a result of external force exerted on the sensing membrane. The changes in the division of optical energy between output fibers 14 may be measured by two photodetectors 17 which provide electrical inputs to a differential amplifier 19. Thus, the output signal of differential amplifier 19 is representative of the force exerted upon medium 15. It will be appreciated that if only one of the input fibers 12 is used to introduce light into the sensor, the other input fiber may be cut short. Alternatively, it may be retained as a backup in the event of a failure of the primary input fiber. It should be noted that, for simplicity, the coupler 11 is shown without the aforementioned fiber twisting in the fusion region. Such twisting is ordinarily preferred, however, to reduce lead sensitivity, which refers to changing of the output light division in response to movement of the input fiber(s).

As compared with other types of fiberoptic sensors, variable coupler sensors offer a uniquely advantageous combination of low cost, relatively simple construction, high performance (e.g., high sensitivity and wide dynamic range), and versatility of application. Other known fiberoptic sensors have used such principles as microbending loss, light phase interference, and polarization rotation by means of birefringence. Fiberoptic micro-bending sensors are designed to sense pressure by excluding light from the fiber in proportion to the changes in pressure. The output light intensity decreases with increases in measured pressure, as pressure is transduced into light loss. Because the measurement accuracy is reduced at lower light levels, the dynamic range of such sensors is severely limited. Interferometric fiberoptic sensors measure changes in pressure by applying pressure to an optical fiber to change its index of refraction. This results in a phase delay that is measured by utilizing a Mach-Zehnder or Michaelson interferometer configuration. These sensors are extremely expensive and require sophisticated modulation techniques that render them unsuitable for many applications. Polarization varying fiberoptic sensors alter the polarization state of a polarized optical signal in accordance with a change in temperature or pressure. Such polarized light sensors require special optical fiber and expensive polarizing beam splitters.

Despite their advantages, conventional variable coupler fiberoptic sensors have been subject to certain limitations inherent in their pre-tensioned linear (straight) coupler design. The conventional design imposes, among other things, significant geometrical limitations. In particular, the size of the sensor must be sufficient to accommodate the fiberoptic leads at both ends of the sensor. The fiberoptic lead arrangement also requires the presence of a clear space around both ends of the sensor in use. Another limitation results from the fact that any displacement of the fusion region necessarily places it under increased tension. At some point of displacement, the tension in the fusion region will become excessive, causing the fusion region to crack or break, with resulting failure of the coupler.

SUMMARY OF THE INVENTION

The present invention provides a sensing pad assembly that uses an improved variable coupler fiberoptic sensor designed to overcome one or more disadvantages of the conventional pre-tensioned linear sensor design. More particularly, the sensor used in the present invention may have an improved design that permits deflection of the coupler fusion region without accompanying tension. The coupler fusion region is preferably arranged substantially in a U-shape, but may more generally be configured as disclosed in co-pending U.S. application Ser. No. 09/316,143 filed May 21, 1999, which is incorporated herein by reference. With a substantially U-shaped configuration, it becomes possible to locate the fiberoptic leads adjacent to each other rather than at opposite ends of the sensor, thus avoiding the earlier discussed geometrical limitations inherent in the conventional pre-tensioned linear coupler design. The pad may be of any desired configuration so long as it can transmit pressure fluctuations to be monitored to the variable coupler fiberoptic sensor. For example, the pad may be in the form of a mattress, a sheet-like member to be placed upon or beneath a mattress, a seat cushion, or a sheet-like member incorporated in a sheet cushion.

In one preferred embodiment of the invention, the sensor is disposed within the internal material of the sensing pad. In another preferred embodiment, the sensor is secured to an outer surface of the pad with its sensing area (containing at least part of the fusion region) coupled to the internal medium of the pad via a hole formed in the pad outer surface. Generally speaking, however, the sensor may be arranged in any manner that couples the sensing area so as to receive pressure fluctuations propagated by the material of the pad.

In summary, according to one of its principal aspects, the present invention provides a sensing pad assembly that comprises a pad member having a surface configured to support an object to be monitored thereon, the pad member being capable of transmitting pressure fluctuations due to acoustic activity or motion of the supported object. The assembly further comprises a variable coupler fiberoptic sensor having a fused-fiber coupling region, with at least a portion of the coupling region being disposed in a sensing area of the sensor and configured such that it can be deflected to change an output of the sensor without the coupling region being put under tension. The sensing area is disposed such that the pressure fluctuations are transmitted thereto to deflect the aforementioned portion of the coupling region and thereby change the output of the sensor in accordance with the pressure fluctuations.

According to another of its principal aspects, the invention provides a sensing pad assembly that comprises a pad member as characterized above, and a variable coupler fiberoptic sensor having a substantially U-shaped, fused-fiber coupling region disposed in a sensing area of the sensor such that the coupling region can be deflected to change the output of the sensor. The sensing area is disposed such that the pressure fluctuations are transmitted thereto to deflect the coupling region and thereby change the output of the sensor in accordance with the pressure fluctuations.

Other aspects of the invention will become apparent from a reading of the following description of the preferred embodiments with reference to the accompanying drawings.

DESCRIPTION OF THE PREFERRED EMBODIMENTS

Figure 3:
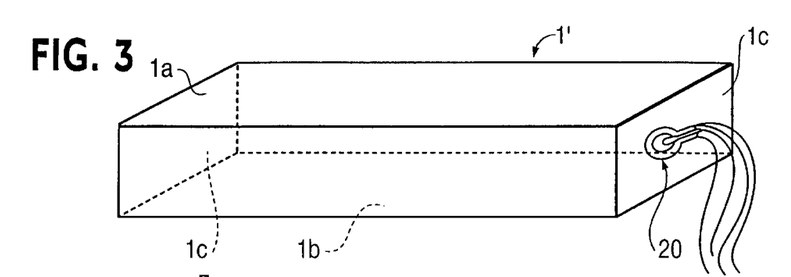
FIG. 3 is a perspective view of a sensor pad assembly according to a first embodiment of the invention.
Figure 4:
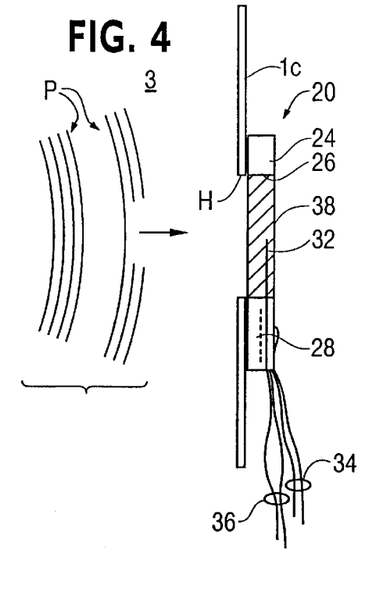
FIG. 4 is a cut-away side view showing, in more detail, the arrangement of the variable coupler fiberoptic sensor in FIG. 3.
Figure 5:
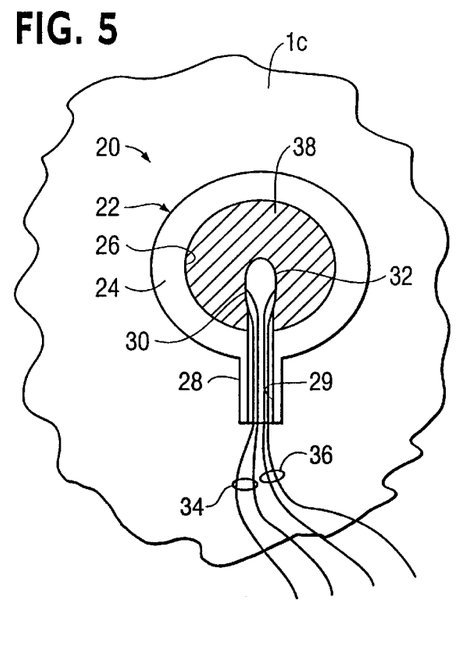
FIG. 5 is a plan view showing the sensor in FIG. 3.

FIGS. 3–5 show a sensing pad assembly according to a first embodiment of the invention. The assembly includes a pad member 1' and a variable coupler fiberoptic sensor 20 attached to an outside surface of the pad member.

The pad member may be of a fluid-filled (e.g., water-filled or air-filled) construction as described in the aforementioned patent to Scanlon. In the form shown, the pad has upper and lower walls 1a and 1b joined by four sidewalls 1c, and is configured to support an object to be monitored on its upper (as viewed) outside surface. Note that only two of the sidewalls 1c are designated in FIG. 3. The object to be monitored may be a human or animal subject, or even a machine, and the dimensions of the pad are suitably selected in consideration of the particular application at hand. For example, in a case of an infant at risk for SIDS, the pad may be constructed as a crib mattress or in a more sheet-like form (say about 2 cm. thick) to be placed on top of a conventional crib mattress. In such case, the pad may be placed beneath a conventional linen sheet and a water-proof sub-sheet to avoid soiling, as well as to protect the infant in the event of leakage from the pad.

In newborn infants, the heart rate is around 120 to 180 beats per minute, or 2–3 Hz, and the respiratory rate is about 60 breaths per minute, or 1 Hz. In adults, the heartbeat occurs at a frequency of about 1 Hz, while breathing occurs at a frequency of about 0.2 Hz. Advantageously, the electrical signal obtained by converting the optical output of the sensor can be filtered to exclude frequencies above, say, 10 Hz, thereby eliminating electrical noise in the EKG domain and other higher frequency noise that may degrade the signal-to-noise ratio.

Depending on the application, the pad member may suitably be gel-filled or even formed of a soft, solid material such as silicone rubber. It is sufficient that the pad be effective to transmit pressure fluctuations due to acoustic activity or motion of the supported object to the variable coupler fiberoptic sensor 20 for detection.

The variable coupler fiberoptic sensor 20 is best seen in FIG. 5. The sensor 20 comprises a support member 22 having a generally circular head portion 24 and a handle-like extension 28. The head portion is formed with a well or through hole to define a circular sensing area 26 of the sensor. A biconical fused tapered coupler 30 is mounted to the support member with at least a portion (here, the entirety) of its fused coupling region 32 disposed in the area 26 and arranged in a U-shape. Input fiber leads 34 and output fiber leads 36 of the coupler are disposed beside one another in a channel 29 formed in the extension 28 and open to the area 26. The leads are manipulated so as to bend the coupling region 32 through 180° into the desired shape and then secured within the channel by a suitable adhesive, such as an epoxy-based glue. The coupling region, which is not under tension, is potted by filling the surrounding well or through hole with elastomer to form a sensing membrane 38 in the known manner—for example, by filling with a silicone rubber such as GE RTV 12. Although four fiber leads are shown, one of the input leads 34 may be cut off after formation of the coupling region 32 if desired, since a single input lead is sufficient for operation of the sensor. The four lead configuration may be preferred, however, since it provides a backup lead that can be used in the event of damage to the primary input lead.

In a practical embodiment of the sensor, the maximum diameter of the membrane may be about the same as that of a nickel coin, but the membrane may be smaller or larger as desired to suit a particular application. The support plate dimensions may be any convenient size, so long as the coupler fusion region and the fiber portions near the fusion region are securely supported. The sensitivity of the device is dependent upon the stiffness of the membrane, as in prior devices.

The sensor 20 is sealingly secured to the pad member 1' adjacent to a hole H through one of the pad sidewalls 1c so as to acoustically couple the sensing membrane 38 to the internal medium 3 of the pad member. The through hole diameter is about the same as that of the sensing membrane 38 to maximize the coupling of the membrane to the internal medium 3. The sensor may be secured about the hole H in any suitable leakproof manner, such as by gluing the head portion 24 to the outer surface of the pad sidewall about the circumference of the hole. Facing the channeled side of the support member 22 away from the pad member, as shown, facilitates reliable sealing to the pad sidewall. The hole H may be used for filling the pad member, or a separate filling port may be provided.

By coupling the sensor membrane 38 to the internal medium 3 of the pad member as shown, pressure fluctuations P caused by movement or by acoustic activity of an object supported on the pad upper surface (e.g., pressure fluctuations due to heartbeat and breathing of a human or animal subject) are transmitted through the medium 3 to the sensing membrane 38. This causes deflection of the membrane 38, and thus of the embedded coupling region 32, in accordance with the pressure fluctuations. As a result, the optical output of the sensor—specifically, the distribution of light in output fibers 36—also changes in accordance with the pressure fluctuations.

Figure 6:
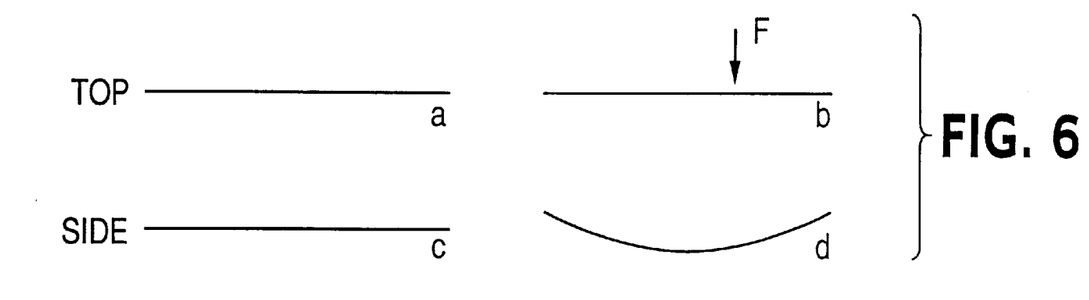
FIG. 6 shows explanatory views (Views 6a–6d) of normal and deflected states of the fusion region of a conventional pre-tensioned linear coupler.
Figure 7:
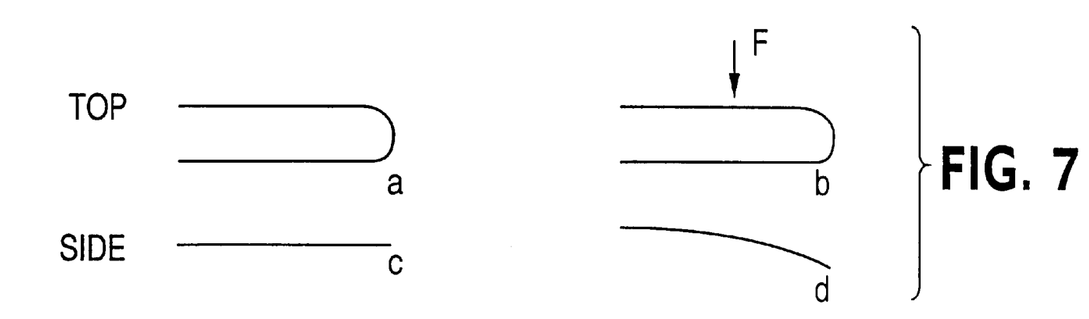
FIG. 7 shows corresponding explanatory views (Views 7a–7d) for a sensor having a U-shaped fusion region.

FIGS. 6 and 7 provide a pictorial comparison between the deflection of a conventional pre-tensioned linear fiberoptic coupler and the deflection of the U-shaped coupler of the sensor in the embodiment of FIGS. 3–5. Views 6a and 6c are top and side views, respectively, showing the fusion region of the conventional coupler in its normal state. Views 6b and 6d are corresponding views of the fusion region being deflected by a downward force F. Views 7a–7d in FIG. 7 are corresponding views to FIG. 6, but show the U-shaped coupler employed in the present invention.

As will be appreciated from View 6d, the deflection of the fusion region in the conventional coupler causes a bowing that tends to stretch and thereby increase the tension on the fusion region. By contrast, the deflection of the U-shaped fusion region in View 7d, which is seen to occur along a direction perpendicular to the plane of the U-shape, merely causes a flexing of the U along its height (horizontal dimension in View 7d), with the fusion region being under substantially no tension. Thus, even large displacements of the fusion region will not cause cracking or breaking.

Figure 8:
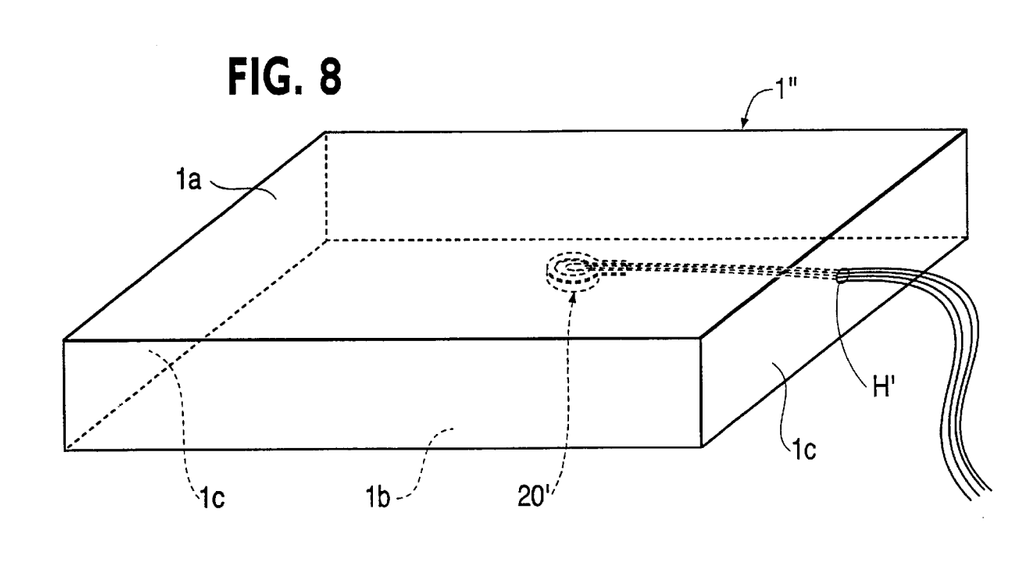
FIG. 8 is a perspective view of a sensor pad assembly according to a second embodiment of the present invention.
Figure 9:
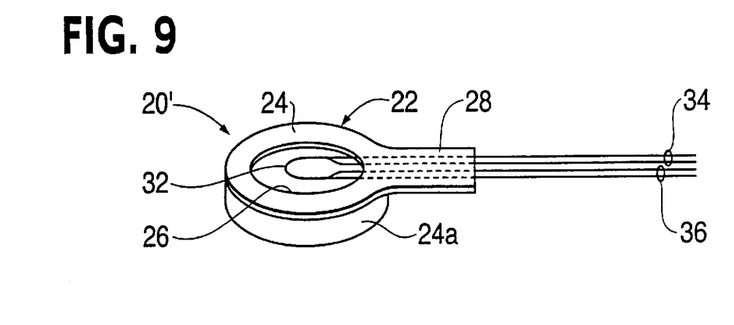
FIG. 9 is a perspective view of the variable coupler fiberoptic sensor used in the embodiment of FIG. 8.

FIGS. 8 and 9 illustrate a sensing pad assembly according to a second embodiment of the invention. In this embodiment, an improved variable coupler fiberoptic sensor 20' is disposed internally of a sensing pad member 1". The sensor 20' and its fiber-optic input and output leads 34, 36 are inserted into through a hole H' in one of the pad sidewalls, which is then sealed with a suitable sealing material. The sensor 20', best seen in FIG. 9, is constructed as an air-backed hydrophone having a construction similar to that of the sensor shown in FIGS. 3–5, except that the sensing membrane 38 is backed by entrapped air that is contained in a hollowed-out cap 24a sealingly attached to the back side (bottom side in FIGS. 8 and 9) of the support member head portion 24. The back (bottom) side of the cap may be secured, as by gluing, to the inner surface of the sensing pad member bottom wall 1b. Alternatively, the sensor 20' may simply be suspended within the pad interior, having a fixed connection only where the fiber leads are secured to the sidewall.

Although not shown in the drawings, it is contemplated that the optical fiber leads in either of the illustrative embodiments would be contained within one or more protective sheaths.

It should be noted that the optical fiber used in the sensors of the present invention is most preferably of very high quality, such as Corning SMF28 which exhibits an optical loss of about 0.18 dB per Km. The photodetectors may be gallium-aluminum-arsenide or germanium detectors for light wavelengths above 900 nm and silicon detectors for shorter wavelengths.

The photodetectors may be connected in either a photovoltaic mode or a photoconductive mode. In the photovoltaic mode, transimpedance amplifiers (which convert current to voltage) may be used to couple the detectors to the differential amplifier inputs. The transimpedance amplifier outputs may also be filtered to eliminate broadband noise. In the photoconductive mode, the detector outputs can be connected to a conventional voltage amplifier. This approach results in more noise, but may be used in applications where cost is a major concern and a lower noise level is not.

It is to be understood, of course, that the foregoing embodiments of the invention are merely illustrative and that other variations are possible in keeping with the basic principles of the invention as described herein.

What is claimed is:

1. A sensing pad assembly, comprising:
 a pad member having a surface configured to support an object to be monitored, said pad member being capable of transmitting pressure fluctuations due to acoustic activity or motion of the supported object; and
 a fiberoptic sensor having a fused-fiber coupling region, at least a portion of said coupling region being curved and being disposed in a sensing area of the sensor and configured such that it can be deflected to change an output of the sensor with said coupling region being put, under substantially tension, said sensing area being disposed such that said pressure fluctuations are transmitted thereto to deflect said portion of said coupling region and thereby change the output of said sensor in accordance with said pressure fluctuations.

2. An assembly according to claim 1, wherein said pad member has an internal medium selected from the group consisting of fluids and gels.

3. An assembly according to claim 2, wherein said sensor is attached to an exterior surface of a wall of said pad member.

4. An assembly according to claim 3, wherein said wall of said pad member has a hole formed therein, with said sensing area being operatively coupled to said internal medium through said hole.

5. An assembly according to claim 4, wherein said sensing area has a sensing membrane encapsulating said portion of said coupling region.

6. An assembly according to claim 4, wherein said sensor includes a support member having a portion surrounding said sensing area and sealingly attached to said wall of said pad member about a perimeter of said hole.

7. An assembly according to claim 6, wherein said sensor has at least one input optical fiber and a plurality of output optical fibers, said input and output optical fibers are connected to said coupling region, and said support member has a surface with channel portions in which said input and output optical fibers are received.

8. An assembly according to claim 7, wherein said support member has an opening in communication with said channel portions and in which said portion of said coupling region is received.

9. An assembly according to claim 2, wherein said sensor is disposed internally of said pad member.

10. An assembly according to claim 9, wherein said sensor includes a support member having a portion bounding said sensing area, and a sensing membrane disposed in said sensing area so as to encapsulate said portion of said coupling region, said sensing area being backed by a hollowed-out cap so as to provide a sealed space adjacent to said sensing membrane.

11. An assembly according to claim 10, wherein said cap is attached to an internal surface of said pad member.

12. An assembly according to claim 10, wherein said sensor is suspended within said internal medium of said pad member.

13. An assembly according to claim 9, wherein said sensor has at least one input optical fiber and a plurality of output optical fibers, said input and output optical fibers are connected to said coupling region, and said support member has a surface with channel portions in which said input and output fibers are received.

14. An assembly according to claim 13, wherein said support member has an opening in communication with said channel portions and in which said portion of said coupling region is received.

15. An assembly according to claim 1, wherein said pad member is formed of resilient solid material.

16. An assembly according to claim 1, wherein said sensor has at least one input optical fiber and a plurality of output optical fibers, and said input and output optical fibers are all connected to said coupling region, said assembly further comprising an electro-optic circuit optically coupled to said plurality of output optical fibers to convert light received from said output optical fibers to an electrical output having a level dependent upon an amount of deflection of said portion of said coupling region.

17. An assembly according to claim 16, wherein said electro-optic circuit comprises a plurality of photodetectors optically coupled to said plurality of output optical fibers, respectively, and a differential amplifier circuit to which outputs of said photodetectors are connected.

18. A sensing pad assembly, comprising:
a pad member having a surface configured to support an object to be monitored, said pad member being capable of transmitting pressure fluctuations due to acoustic activity or motion of the supported object; and
a fiberoptic sensor having a substantially U-shaped, fused-fiber coupling region disposed in a sensing area of said sensor such that said coupling region can be deflected to change an output of said sensor, said sensing area being disposed such that said pressure fluctuations are transmitted thereto to deflect said coupling region and thereby change the output of said sensor in accordance with said pressure fluctuations.

19. An assembly according to claim 18, wherein said pad member has an internal medium selected from the group consisting of fluids and gels.

20. An assembly according to claim 19, wherein said sensor is attached to an exterior surface of said pad member.

21. An assembly according to claim 20, wherein said sensor is mounted to a wall of said pad member having a hole formed therein, with said sensing area being operatively coupled to said internal medium through said hole.

22. An assembly according to claim 21, wherein said sensing area has a sensing membrane encapsulating said portion of said coupling region.

23. An assembly according to claim 21, wherein said sensor includes a support member having a portion surrounding said sensing area and sealingly attached to said wall of said pad member about a perimeter of said hole.

24. An assembly according to claim 23, wherein said sensor has at least one input optical fiber and a plurality of output optical fibers, said input and output optical fibers are connected to said coupling region, and said support member has a surface with channel portions in which said input and output optical fibers are received.

25. An assembly according to claim 24, wherein said support member has an opening in communication with said channel portions and in which said coupling region is received.

26. An assembly according to claim 19, wherein said sensor is disposed internally of said pad member.

27. An assembly according to claim 26, wherein said sensor includes a support member having a portion bounding said sensing area, and a sensing membrane disposed in said sensing area so as to encapsulate said portion of said coupling region, said sensing area being backed by a hollowed-out cap so as to provide a sealed space adjacent to said sensing membrane.

28. An assembly according to claim 27, wherein said cap is affixed to an internal surface of said pad member.

29. An assembly according to claim 27, wherein said sensor is suspended within said internal medium of said pad member.

30. An assembly according to claim 26, wherein said sensor has at least one input optical fiber and a plurality of output optical fibers, said input and output optical fibers are connected to said coupling region, and said support member has a surface with channel portions in which said input and output optical fibers are received.

31. An assembly according to claim 30, wherein said support member has an opening in communication with said channel portions and in which said coupling region is received.

32. An assembly according to claim 18, wherein said pad member is formed of resilient solid material.

33. An assembly according to claim 18, wherein said sensor has at least one input optical fiber and a plurality of output optical fibers, said input and output optical fibers are connected to said coupling region, said assembly further comprising an electro-optic circuit optically coupled to said plurality of output optical fibers to convert light received from said output optical fibers to an electrical output having a level dependent upon an amount of deflection of said coupling region.

34. An assembly according to claim 33, wherein said electro-optic circuit comprises a plurality of photodetectors optically coupled to said plurality of output optical fibers, respectively, and a differential amplifier circuit to which outputs of said photodetectors are connected.

35. A sensing pad assembly, comprising:
a pad member having a surface configured to support an object to be monitored, said pad member being capable of transmitting pressure fluctuations due to acoustic activity or motion of the supported object; and
a fiberoptic sensor having a fused-fiber coupling region, with at least a portion of said coupling region being curved and disposed substantially in a plane in a sensing area of the sensor and being configured such that it can be deflected along a direction perpendicular to said plane to change an output of the sensor with said coupling region being under substantially no tension, said sensing area being disposed such that said pressure fluctuations are transmitted thereto to deflect said portion of said coupling region along said direction perpendicular to said plane and thereby change the output of said sensor in accordance with said pressure fluctuations.

36. An assembly according to claim 35, wherein said pad member has an internal medium selected from the group consisting of fluids and gels.

37. An assembly according to claim 36, wherein said sensor is attached to an exterior surface of a wall of said pad member.

38. An assembly according to claim 37, wherein said wall of said pad member has a hole formed therein, with said sensing area being operatively coupled to said internal medium through said hole.

39. An assembly according to claim 38, wherein said sensing area has a sensing membrane encapsulating said portion of said coupling region.

40. An assembly according to claim 38, wherein said sensor includes a support member having a portion surrounding said sensing area and sealingly attached to said wall of said pad member about a perimeter of said hole.

41. An assembly according to claim 40, wherein said sensor has at least one input optical fiber and a plurality of output optical fibers, said input and output optical fibers are connected to said coupling region, and said support member has a surface with channel portions in which said input and output optical fibers are received.

42. An assembly according to claim 41, wherein said support member has an opening in communication with said channel portions and in which said portion of said coupling region is received.

43. An assembly according to claim 36, wherein said sensor is disposed internally of said pad member.

44. An assembly according to claim 43, wherein said sensor includes a support member having a portion bounding said sensing area, and a sensing membrane disposed in said sensing area so as to encapsulate said portion of said coupling region, said sensing area being backed by a hollowed-out cap so as to provide a sealed space adjacent to said sensing membrane.

45. An assembly according to claim 44, wherein said cap is attached to an internal surface of said pad member.

46. An assembly according to claim 44, wherein said sensor is suspended within said internal medium of said pad member.

47. An assembly according to claim 43, wherein said sensor has at least one input optical fiber and a plurality of output optical fibers, said input and output optical fibers are connected to said coupling region, and said support member has a surface with channel portions in which said input and output fibers are received.

48. An assembly according to claim 47, wherein said support member has an opening in communication with said channel portions and in which said portion of said coupling region is received.

49. An assembly according to claim 35, wherein said pad member is formed of resilient solid material.

50. An assembly according to claim 35, wherein said sensor has at least one input optical fiber and a plurality of output optical fibers, and said input and output optical fibers are all connected to said coupling region, said assembly further comprising an electro-optic circuit optically coupled to said plurality of output optical fibers to convert light received from said output optical fibers to an electrical output having a level dependent upon an amount of deflection of said portion of said coupling region.

51. An assembly according to claim 50, wherein said electro-optic circuit comprises a plurality of photodetectors optically coupled to said plurality of output optical fibers, respectively, and a differential amplifier circuit to which outputs of said photodetectors are connected.

52. A sensing pad assembly comprising:
a pad member having a surface configured to support an object to be monitored, said pad member being capable of transmitting pressure fluctuations due to acoustic activity or motion of the supported object; and
a fiberoptic sensor having a substantially U-shaped, fused-fiber coupling region disposed substantially in a plane in a sensing area of said sensor such that said coupling region can be deflected along a direction perpendicular to said plane to change an output of said sensor, said sensing area being disposed such that said pressure fluctuations are transmitted thereto to deflect said coupling region along said direction perpendicular to said plane and thereby change the output of said sensor in accordance with said pressure fluctuations.

53. An assembly according to claim 32, wherein said pad member has an internal medium selected from the group consisting of fluids and gels.

54. An assembly according to claim 53, wherein said sensor is attached to an exterior surface of said pad member.

55. An assembly according to claim 54, wherein said sensor is mounted to a wall of said pad member having a hole formed therein, with said sensing area being operatively coupled to said internal medium through said hole.

56. An assembly according to claim 55, wherein said sensing area has a sensing membrane encapsulating said portion of said coupling region.

57. An assembly according to claim 55, wherein said sensor includes a support member having a portion surrounding said sensing area and sealingly attached to said wall of said pad member about a perimeter of said hole.

58. An assembly according to claim 57, wherein said sensor has at least one input optical fiber and a plurality of output optical fibers, said input and output optical fibers are connected to said coupling region, and said support member has a surface with channel portions in which said input and output optical fibers are received.

59. An assembly according to claim 58, wherein said support member has an opening in communication with said channel portions and in which said coupling region is received.

60. An assembly according to claim 53, wherein said sensor is disposed internally of said pad member.

61. An assembly according to claim 60, wherein said senor includes a support member having a portion bounding said sensing area, and a sensing membrane disposed in said sensing area so as to encapsulate said portion of said coupling region, said sensing area being backed by a hollowed-out cap so as to provide a sealed space adjacent to said sensing membrane.

62. An assembly according to claim 61, wherein said cap is affixed to an internal surface of said pad member.

63. An assembly according to claim 61, wherein said sensor is suspended within said internal medium of said pad member.

64. An assembly according to claim 60, wherein said sensor has at least one input optical fiber and a plurality of output optical fibers, said input and output optical fibers are connected to said coupling region, and said support member has a surface with channel portions in which said input and output optical fibers are received.

65. An assembly according to claim 64, wherein said support member has an opening in communication with said channel portions and in which said coupling region is received.

66. An assembly according to claim 52, wherein said pad member is formed of resilient solid material.

67. An assembly according to claim 52, wherein said sensor has at least one input optical fiber and a plurality of output optical fibers, said input and output optical fibers are connected to said coupling region, said assembly further comprising an electro-optic circuit optically coupled to said plurality of output optical fibers to convert light received from said output optical fibers to an electrical output having a level dependent upon an amount of deflection of said coupling region.

68. An assembly according to claim 67, wherein said electro-optic circuit comprises a plurality of photodetectors optically coupled to said plurality of output optical fibers, respectively, and a differential amplifier circuit to which outputs of said photodetectors are connected.

* * * * *